United States Patent [19]

Schinohara et al.

[11] 4,209,378

[45] Jun. 24, 1980

[54] OXYGEN SENSING ELEMENT

[75] Inventors: Hiroshi Schinohara, Okazaki; Yasuhiro Otsuka, Toyota; Shinichi Matsumoto, Toyota; Toshinobu Furutani, Toyota; Hiroshi Wakizaka, Toyota, all of Japan

[73] Assignee: Toyota Jidosha Kogyo Kabushiki Kaisha, Toyota, Japan

[21] Appl. No.: 36,379

[22] Filed: May 4, 1979

[30] Foreign Application Priority Data

Aug. 8, 1978 [JP] Japan .................................. 53-95778

[51] Int. Cl.$^2$ .......................................... G01N 27/58
[52] U.S. Cl. ................................................. 204/195 S
[58] Field of Search ............. 204/195 S, 1 S; 422/98; 324/29

[56] References Cited

U.S. PATENT DOCUMENTS

| | | | |
|---|---|---|---|
| 3,576,730 | 4/1971 | Spacil | 204/195 S |
| 4,045,319 | 8/1977 | Deportes et al. | 204/195 S |
| 4,152,232 | 5/1979 | Otsuka et al. | 204/195 S |
| 4,155,828 | 5/1979 | Takao et al. | 204/195 S |

Primary Examiner—G. L. Kaplan
Attorney, Agent, or Firm—Kenyon & Kenyon

[57] ABSTRACT

Low temperature operability of an oxygen sensing element, which comprises a solid electrolyte member composed of sintered material, and a means for providing a reference oxygen partial pressure, composed of a sintered product of a finely divided metal or metal-metal oxide mixture powder and being completely embedded within the solid electrolyte member, is improved by the incorporation of from 0.5 to 10% by weight, based on the total weight of the sintered product, of a finely divided platinum group metal powder in the sintered product of the reference oxygen partial pressure-providing means.

9 Claims, 6 Drawing Figures

OXYGEN SENSING ELEMENT

BACKGROUND OF THE INVENTION

This invention relates to an oxygen sensing element capable of measuring partial pressures of oxygen in sample gases. More particularly, it relates to an oxygensensing element suitable for use in an exhaust gas purifying system wherein the contact of oxygen in an exhaust gas from an automobile internal combustion engine is measured, thereby to determine the content of unburnt hydrocarbons, carbon monoxide and nitrogen oxides in the exhaust gas and, based on the measurement results, the air-fuel ratio is appropriately adjusted so that the efficiency of a catalyst for purifying the exhaust gas is enhanced; or suitable for use in a device for measuring the concentration of oxygen in a molten metal in the course of metal refining.

An oxygen sensor is an oxygen concentration cell having a structure such that electrodes are mounted on the opposite sides of a solid electrolyte composed of a sintered ceramic material capable of conducting an oxygen ion. An electromotive force is produced across the solid electrolyte by the difference between the partial pressures of oxygen in reference and sample gases contacting opposite sides of the solid electrolyte. The concentration of oxygen in the sample gas can be determined by measuring the electromotive force so produced. That is, as is well known, assuming that the partial pressures of oxygen in the reference and sample gases are $PO_2(1)$ and $PO_2(2)$, respectively, the electromotive force E produced between the electrodes on the opposite sides of the solid electrolyte is expressed by the following equation.

$$E = \frac{RT}{4F} \ln \frac{PO_2(1)}{PO_2(2)}$$

wherein R is gas constant, T is absolute temperature and F is Faraday's constant. Thus, if the partial pressure of oxygen $PO_2(1)$ in the reference gas is known, the partial pressure of oxygen $PO_2(2)$ in the sample gas can be determined from the above-mentioned equation by measuring the electromotive force E. Conventionally, air is used as the reference gas. The reference gas may also be generated chemically by using a mixture of a metal and its oxide which produces an equilibrium partial pressure of oxygen. This reference gas-generating metal-metal oxide mixture is hereinafter referred to as "reference solid electrode" for brevity.

However, the conventional oxygen sensors, wherein the reference solid electrode of a metal-metal oxide mixture is employed, are not advantageous compared with the oxygen sensors wherein air is used as the reference gas. This is because the former oxygen sensors do not successfully operate at a low temperature. That is, at a temperature lower than about 400° C., the former oxygen sensors generate little or no electromotive force and the internal impedance thereof is undesirably increased together with an apparent reduction of the electromotive force. In order to overcome this defect, it has been proposed to provide an electrode layer on the interface between the metal-metal oxide mixture reference solid electrode and the solid electrolyte, which electrode layer is composed of an electrochemically active metal such as platinum. The electrode layer accelerates the conversion of oxygen ions to molecular or atomic oxygen according to the following formula and, thus, reduces the polarization occurring in the metal-metal oxide mixture.

$$20^{--} \rightarrow O_2(\text{or } 2O) + 4e^-$$

Such as electrode layer is formed by chemical or electrical plating, ion-plating or the like. However, the formation of such an electrode layer is complicated, and it is difficult to avoid a variability of some performances such as the operating temperature, the response time and the internal resistance among the resulting oxygen sensors.

Japanese Patent Publication (KOKAI) No. 9497/1976 discloses an oxygen sensing electrochemical cell having a structure such that a reference solid electrode of a metal-metal oxide mixture is completely enclosed within a solid electrolyte member having an electrode mounted on the exterior surface thereof. This oxygen sensing electrochemical cell does not have such a defect as is encountered in the above-mentioned oxygen sensing cell provided with an electrochemically active metal electrode layer on the boundary between the metal-metal oxide mixture reference medium and the solid electrolyte. This cell is, however, still not satisfactory in its operability at a low temperature.

SUMMARY OF THE INVENTION

The main object of the present invention is to provide improved oxygen sensing elements which exhibit a reduced internal impedance and a satisfactory low temperature operability and are capable of being manufactured without a substantial variability of performances among the resulting oxygen sensing elements.

Other objects and advantages of the present invention will be apparent from the following description.

In accordance with the present invention, there is provided an improvement in an oxygen sensing element which comprises a solid electrolyte member composed of sintered material, and a means for providing a reference partial pressure of oxygen, composed of a sintered product of a finely divided metal or metal-metal oxide mixture powder; the reference oxygen partial pressure-providing means being completely embedded within the solid electrolyte member and having a lead-out wire connected thereto, and the solid electrolyte member having an electrode or electrodes mounted on the exterior surface thereof. The improvement of the present invention resides in the fact that the sintered product of the reference oxygen partial pressure-providing means has dispersed therein a minor amount of a finely divided platinum group metal powder.

BRIEF DESCRIPTION OF THE DRAWINGS

The invention will be described in detail by way of examples with reference to the accompanying drawings in which.

DETAILED DESCRIPTION OF THE PREFERRED EMBODIMENT

Figure 1:
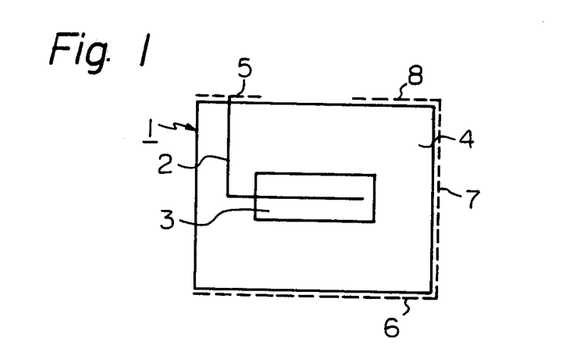
FIG. 1 illustrates a schematic section of an embodiment of the oxygen sensing element of the invention.

Referring to FIG. 1 there is illustrated a schematic section of an embodiment of the oxygen sensing element of the invention. The oxygen sensing element 1 has a means 3 for providing a reference partial pressure of oxygen, composed of a sintered body of a finely divided metal or metal-metal oxide mixture powder, i.e. a reference solid electrode. The reference solid electrode 3 is totally embedded within a solid electrolyte member 4, and has an electrode lead-out wire 2 connected thereto, made of a thermally resistant electroconductive metal such as platinum or a platinum-rhodium alloy. The solid electrolyte member 4 has metal electrodes 5 and 6 on the exterior surface thereof. The electrode 5 is an auxiliary electrode for transmitting therethrough an output signal from the reference solid electrode 3 to an electrical measuring circuit (not shown in FIG. 1). The electrode 6 is a porous metal electrode to be exposed to a sample gas. Electrode lead 7–8 is intended to transmit therethrough an output signal from the electrode 6 to the electrical measuring circuit. The oxygen sensing element 1 may be of any desired shape, such as, for example, a disc, column, sphere or parallelopiped. Of these, a disc and column are desirable.

The solid electrolyte member 4 may be composed of a solid electrolyte material conventionally used in oxygen concentration cells, such as zirconia ($ZrO_2$). The solid electrolyte material is preferably a solid solution prepared by incorporating a minor amount of $Y_2O_3$, CaO or MgO followed by sintering. An optimum solid electrolyte material is comprised of a sintered zirconia composition having incorporated therein 5 to 10% by mole of $Y_2O_3$.

The reference solid electrode 3 is a sintered product of a finely divided metal or metal-metal oxide mixture powder. Even when the reference solid electrode is not made of a metal-metal oxide mixture but only metal, it can provide a reference partial pressure of oxygen, because the reference solid electrode accepts oxygen ions transmitted through the solid electroyte material during the operation of the oxygen sensing element and, thus, the metal is partially converted into metal oxide. The metal ingredients used for the preparation of the reference solid electrode include, for example, iron, molybdenum, chromium, tungsten, nickel, cobalt, silicon and manganese.

The reference solid electrode 3 employed in the oxygen sensing element of the invention is characterized as being composed of the sintered product of a finely divided metal or metal-metal oxide mixture composition having incorporated therein a finely divided platinum group metal in an amount of from 0.5 to 10% by weight, preferably from 1.0 to 5.0% by weight, based on the total weight of the sintered product. When the amount of the platinum group metal is less than about 0.5% by weight, the intended purpose cannot be achieved. In contrast, when the amount of the platinum group metal exceeds about 10% by weight, the manufacturing cost increases, and both the reduction of the internal impedance and the improvement of the low temperature operability are not in proportion to the increase in the amount of the incorporated platinum group metal.

The platinum group metal includes, for example, platinum, rhodium, palladium and iridium. These metals may be used either alone or in combination. Of these metals platinum is preferable. A mixture of from 1.0 to 5.0% by weight, based on the weight of the reference solid electrode, of platinum, and not more than 2.0% by weight, particularly from 0.1 to 0.5% by weight, based on the weight of the reference solid electrode, of rhodium is more preferable.

It is presumed that the platinum group metal dispersed in the reference solid electrode catalytically accelerates the electrode reaction, i.e., the conversion of oxygen ions, transmitted through the solid electrolyte, into molecular or atomic oxygen due to the oxidative effect of the metal constituting the reference solid electrode. Thus, the oxygen sensing element of the present invention exhibits a reduced internal impedance and a good low temperature operability, which are comparable with ormore satisfactory than those of the conventional oxygen sensing element having an electrode layer of an electrochemically active metal on the interface between the reference solid electrode and the solid electrolyte. Furthermore, the oxygen sensing element of the invention has a simple structure and exhibits little or no variability of performances such as the operating temperature, the response time and the internal resistance.

Figure 2:
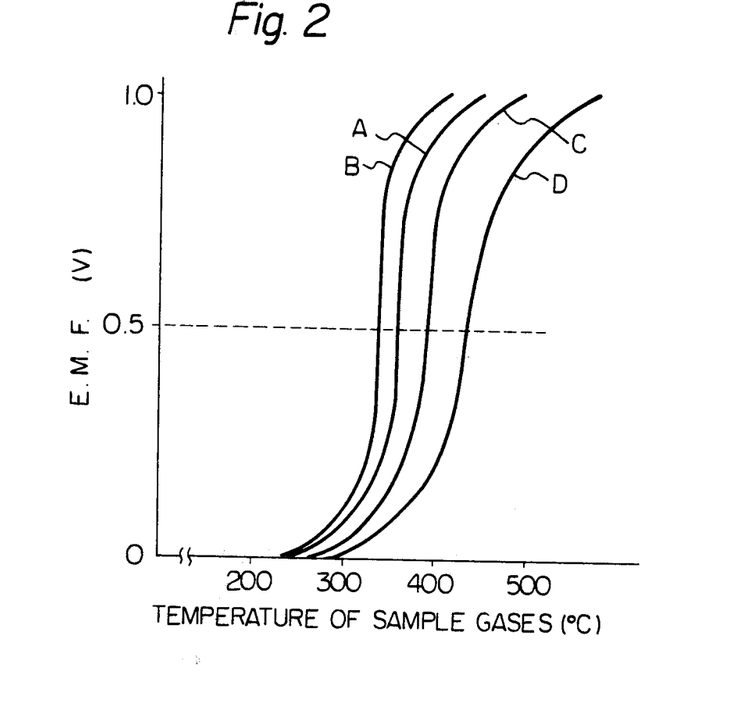
FIG. 2 is a graph showing the dependence of the electromotive force (E.M.F.) of oxygen sensing elements upon the operating temperature.

Referring to FIG. 2, there is disclosed a graph showing the dependence of the electromotive force upon the temperature of a sample gas. The ordinate and the abscissa represent the electromotive force in volts and the temperature of a sample gas in °C., respectively. In FIG. 2, curves A and B correspond to the oxygen sensing elements of the invention (the reference solid electrodes of A and B have dispersed therein, respectively, 1.0% by weight of platinum and a mixture of 1.0% by weight of platinum and 0.1% by weight of rhodium). Curves C and D correspond to, respectively, an oxygen sensing element having a reference solid electrode having no platinum group metal dispersed therein and an oxygen sensing element utilizing air as the reference gas. Apparently, the oxygen sensing elements of the invention (curves A and B) are advantageous over the conventional ones (curves C and D) in operability in a low temperature region.

Figure 3:
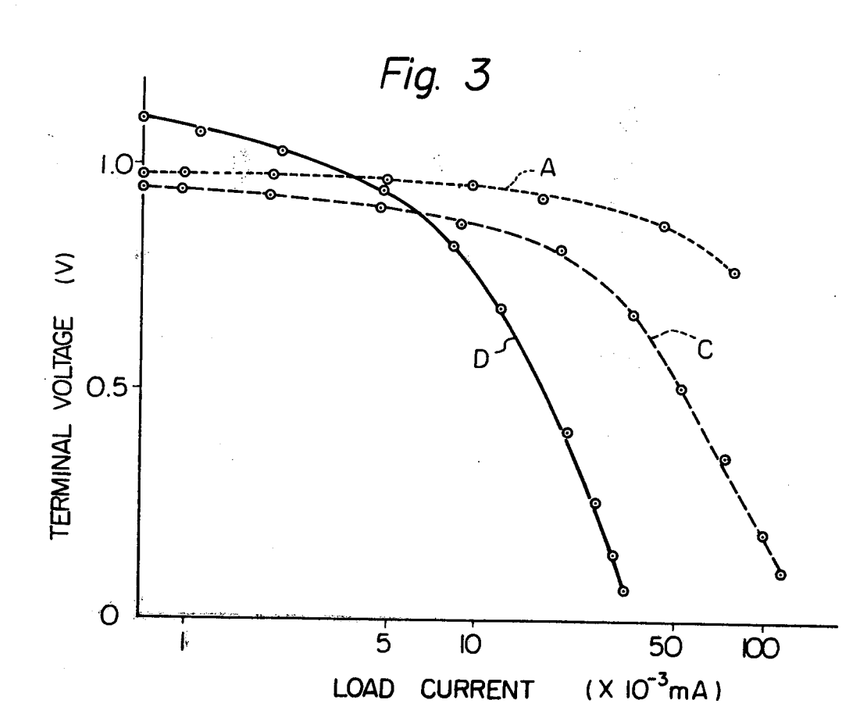
FIG. 3 is a graph showing the relationship of load current to terminal voltage of oxygen sensing elements.

FIG. 3 is a graph showing the relationship of load current to terminal voltage of oxygen sensing elements. The ordinate and the abscissa represent the terminal voltage (volt) and the load current ($\times 10^{-3}$ mA), respectively. Curves A, B, C and D correspond to oxygen sensing elements identical to those mentioned with reference to FIG. 2. These curves show that the terminal voltage of the oxygen sensing elements of the invention (curves A and B) decrease to a lesser extent as the load current increases, than the conventional, oxygen sensing elements (curves C and D) decrease.

The results shown in FIGS. 2 and 3 were obtained on oxygen sensing elements each having a reference solid electrode made of a iron-iron oxide mixture. However, approximately similar tendencies were observed on oxygen sensing elements each having a reference solid electrode made of another metal-metal oxide mixture.

The reference solid electrode may preferably contain, in addition to the metal or metal-metal oxide mixture ingredient and the platinum group metal ingredient, an appropriate amount of an antisintering material. The antisintering material used includes, for example, stabilized zirconia, which is usually identical to that used for the solid electrolyte material, and alumina, alumina-magnesia, silica and alumina-silica. These antisintering materials may be used either alone or in combination. The amount of the antisintering material may be in the range of from 5 to 70% by weight based on the total weight of the reference solid electrode. By the incorporation of the antisintering material, it can be avoided that the reference solid electrode is sintered to an excessive degree in the sintering step, and the thermal shrinkage of the reference solid electrode can be made to be the same as that of the solid electrolyte. Thus, the distortion of the oxygen sensing element and the separation of electrodes therefrom can be completely avoided.

The oxygen sensing element of the present invention is manufactured in various ways. For example, a finely divided metal or metal-metal oxide mixture powder having incorporated therein predetermined amounts of a platinum group metal and optional, other additives is press-molded to form a reference solid electrode. Then, the reference solid electrode is encapsulated within a solid electrolyte member by forming the solid electrolyte member on the exterior surface of the reference solid electrode by vapor deposition, ion plating, sintering and sputtering, as disclosed in Japanese Patent Publication (KOKAI) No. 9497/1976. Finally, the so formed product is sintered.

In another more preferable technique, a part of the amount of a finely divided solid electrolyte material, required for the formation of the solid electrolyte member is press-molded to form a provisional solid electrolyte member having a hole in which a reference solid electrode is to be formed. Then, a predetermined amount of a finely divided metal or metal-metal oxide mixture composition having incorporated therein a platinum group metal and optional other additives is charged in the hole of the provisional solid electrolyte member followed by pressing the charged composition. In the recess of the provisional solid electrolyte member, formed by the pressing of the charged composition, the remaining part of the finely divided solid electrolyte material is heaped up. Then the heaped-up material is pressed to obtain a structure such that the reference solid electrode is completely encapsulated or embedded within the solid electrolyte member. Finally, the obtained structure is sintered.

The mounting of the external electrode or electrodes on the exterior surface of the solid electrolyte member may be carried out by a conventional technique such as paste coating and baking, electrical or chemical plating or ion plating.

It is preferable that the porous external electrode 6 (FIG. 1) to be exposed to a sample gas be coated with a porous layer having a magnesium spinel structure or another spinel structure composed of a thermal resistant metal oxide. Such a porous layer minimizes the deterioration of the porous external electrode caused by the phosphorus, lead and sulfur present in the exhaust gas from an automobile.

The oxygen sensing element of the invention is advantageously used for measuring the content of oxygen, for example, in an exhaust gas from an automobile internal combustion engine or in a molten metal in the course of metal refining. It is particularly suitable for use in an exhaust gas purifying system wherein the content of oxygen in an exhaust gas from an automobile internal combustion engine is measured, thereby to determine the content of unburnt hydrocarbons, carbon monoxide and nitrogen oxides in the exhaust gas, and based on the measurement results, the air-fuel ratio is appropriately adjusted so that the efficiency of a catalyst for purifying the exhaust gas is enhanced.

Figure 4A:
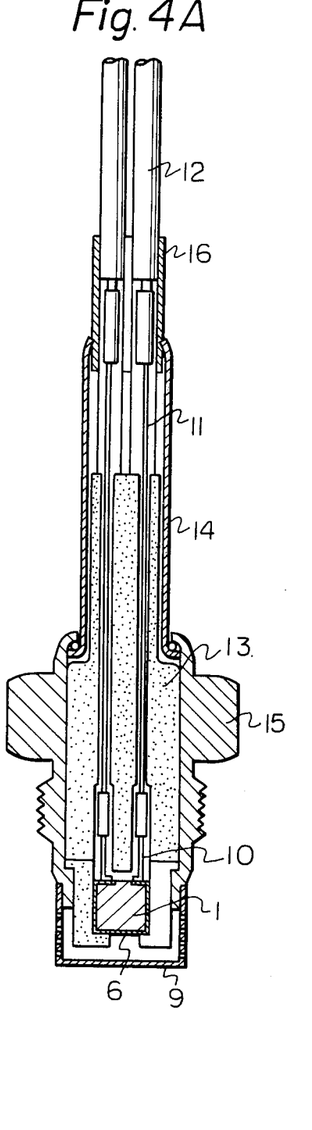
FIGS. 4A and 4B illustrate a vertical section and a partial section side elevation, respectively, of an embodiment of the oxygen sensor device for use in automobiles.
Figure 4B:
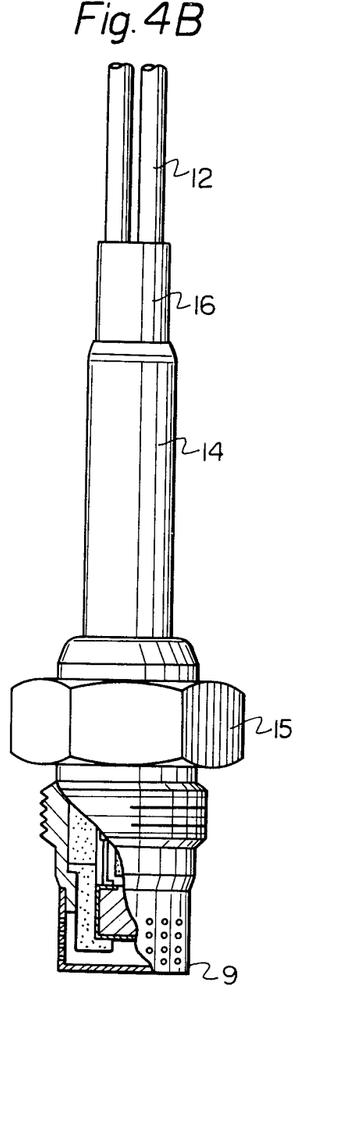

Referring to FIGS. 4A and 4B there is disclosed an embodiment of the oxygen sensor device useful for measuring the content of oxygen in an exhaust gas from an automobile internal combustion engine. The oxygen sensor device is fitted to the exhaust manifold in a manner such that the external platinum electrode 6 of an oxygen sensing element 1 is exposed to the exhaust gas. A casing 9 for protecting the oxygen sensing element 1 has a plurality of perforations through which the exhaust gas is allowed to flow. The output signals are transmitted from the respective electrodes through lead-out wires such as a platinum lead and to an electrical measuring circuit (not shown in FIGS. 4A and 4B). The output signal-taking out mechanism is electrically protected by an alumina tube 13, a Teflon tube 16 and an insulative tube 12 and is mechanically protected by metallic tubular members 14 and 15.

The invention will be further illustrated by way of the following examples.

EXAMPLE 1

A mixture comprised of 70% by weight of a commercially available carbonyl iron powder and 30% by weight of an alpha-A1203 powder was uniformly blended with 1% by weight, based on the weight of the mixture, of a platinum powder of 325 mesh in particle size. One end of a platinum lead-out wire having a diameter of 0.5 mm was inserted into a mass of the platinum-added blend. Then, the blend was compression molded into a pellet of a columnar shape by using a hand press. The pellet was encapsulated with a ZrO2 powder having incorporated therein 8% by mole of Y203. The ZrO2 encapsulated pellet was pressed into a pellet of columnar shape by using a hand press. The so obtained pellet was sintered in an electric oven at a temperature of 1,400° C. for three hours while a hydrogen (1% by volume)-argon (99% by volume) gaseous mixture was introduced in the oven at a rate of 1 liter/min. The upper and lower flat surfaces of the sintered columnar pellet were abraded by using a number 250 abrasive paper and degreased, and then, coated with a platinum paste, as illustrated in FIG. 1. The platinum paste-coated pellet was baked in an electric oven at a temperature of 600° C. for 10 minutes to obtain an oxygen sensing element having external platinum electrodes mounted on the exterior surface thereof.

Electromotive force characteristics of the oxygen sensing element were evaluated as follows. The oxygen sensing element was fitted to a tube in a manner such that one of the external electrodes of the element was exposed to the inner atmosphere of the tube. A gaseous mixture of 1% by volume of oxygen and 99% by volume of nitrogen was introduced into the tube at a rate of 2,000 ml/min. and a load of 1M ohm was imparted to the electrode, while the temperature of the gaseous mixture was elevated at a rate of 10° C./min. The dependence of the electromotive force of the oxygen sensing element upon the temperature of the element was determined by using a DC voltmeter having an input impedance of 1,000 M ohm. The results are shown in FIG. 2 (curve A) and Table I, below.

EXAMPLE 2

By a procedure similar to that mentioned in Example 1, an oxygen sensing element was manufactured and its electromotive force characteristics were evaluated. In this procedure, a mixture of 1% by weight of a platinum powder and 0.1% by weight of a rhodium powder was employed instead of 1% by weight of a platinum powder. The results are shown in FIG. 2 (curve B) and Table I, below.

COMPARATIVE EXAMPLE 1

By a procedure similar to that mentioned in Example 1, an oxygen sensing element was manufactured and its electromotive force characteristics were evaluated. In this procedure, no platinum powder was added to the carbonyl iron-alpha-alumina mixture. The results are shown in FIG. 2 (curve C) and Table I, below.

COMPARATIVE EXAMPLE 2

A zirconia powder stabilized with 8% by mole of $Y_2O_3$ was molded to obtain a cup-shaped solid electrolyte member. Two platinum electrode layers of about one micron in thickness were formed on both surfaces of the solid electrolyte member by chemical plating and then electrical plating. A porous spinel ($Al_2O_3 \cdot MgO$) coating layer of about 80 microns in thickness was formed by a conventional procedure on one of the platinum electrode layers to be exposed to a sample gas.

The electromotive force characteristics of the so obtained oxygen sensing element were evaluated by a procedure similar to that mentioned in Example 1, wherein a gaseous mixture of 1% by volume of hydrogen and 99% by volume of nitrogen was employed as a sample gas. The results are shown in FIG. 2 (curve D) and Table I, below.

EXAMPLES 3 through 16 and Comparative Examples 3 through 9

By a procedure similar to that mentioned in Example 1, oxygen sensing elements were manufactured and their electromotive force characteristics were evaluated. In this procedure, various mixtures comprised of 70% by weight of a metal selected from molybdenum, chromium, tungsten, nickel, cobalt, silicon and manganese and 30% by weight of alpha-alumina were employed instead of the carbonyl iron-alpha-alumina mixture. The results are shown in Table I, below.

Table I

| Ex. and Com. Ex. *1 | Composition of reference solid electrode | | | | Temperature off element (°C.) *3 |
|---|---|---|---|---|---|
| | Metal *2 | Anti-sintering material | Platinum group metal (wt. %) | | |
| | | | Pt | Rh | |
| C 2 | —*4 | — | — | — | 437 |
| C 1 | Fe | α-Al₂O₃ 30 wt% | — | — | 395 |
| E 1 | Fe | α-Al₂O₃ 30 wt% | 1.0 | — | 362 |
| E 2 | Fe | α-Al₂O₃ 30 wt% | — | 0.1 | 341 |
| C 3 | Mo | α-Al₂O₃ 30 wt% | — | — | 392 |
| E 3 | Mo | α-Al₂O₃ 30 wt% | 1.0 | — | 368 |
| E 4 | Mo | α-Al₂O₃ 30 wt% | — | 0.1 | 345 |
| C 4 | Cr | α-Al₂O₃ 30 wt% | — | — | 387 |
| E 5 | Cr | α-Al₂O₃ 30 wt% | 1.0 | — | 358 |
| E 6 | Cr | α-Al₂O₃ 30 wt% | — | 0.1 | 342 |
| C 5 | W | α-Al₂O₃ 30 wt% | — | — | 386 |
| E 7 | W | α-Al₂O₃ 30 wt% | 1.0 | — | 361 |
| E 8 | W | α-Al₂O₃ 30 wt% | — | 0.1 | 350 |
| C 6 | Ni | α-Al₂O₃ 30 wt% | — | — | 402 |
| E 9 | Ni | α-Al₂O₃ 30 wt% | 1.0 | — | 385 |
| E10 | Ni | α-Al₂O₃ 30 wt% | — | 0.1 | 364 |
| C 7 | Co | α-Al₂O₃ 30 wt% | — | — | 395 |
| E11 | Co | α-Al₂O₃ 30 wt% | 1.0 | — | 366 |
| E12 | Co | α-Al₂O₃ 30 wt% | — | 0.1 | 345 |
| C 8 | Si | α-Al₂O₃ 30 wt% | — | — | 410 |
| E13 | Si | α-Al₂O₃ 30 wt% | 1.0 | — | 387 |
| E14 | Si | α-Al₂O₃ 30 wt% | — | 0.1 | 363 |
| C 9 | Mn | α-Al₂O₃ 30 wt% | — | — | 386 |
| E15 | Mn | α-Al₂O₃ 30 wt% | 1.0 | — | 367 |
| E16 | Mn | α-Al₂O₃ 30 wt% | — | 0.1 | 351 |

*1 C: Comparative Example, E: Example
*2 Metal used in the metal-metal oxide mixture
*3 Temperature of oxygen sensing element when the oxygen sensing element generated an electromotive force equal to one half of the maximum electromotive force.
*4 Reference gas is air It will be apparent from Table I and FIG. 2 that the oxygen sensing element of the invention exhibits improved low temperature operability, i.e., can produce a normal signal even in a low temperature region. Thus, when the oxygen sensing element of the invention is used in an exhaust gas purification system of an automobile internal combustion engine, the exhaust gas purification system starts the normal operation with a high accuracy immediately after the automobile engine starts to be driven.

EXAMPLE 17

This example illustrates the effect of an antisintering agent (alpha-$Al_2O_3$) upon the high temperature durability of the oxygen sensing element.

By a procedure similar to that mentioned in Example 1, oxygen sensing elements were manufactured wherein the following four compositions were separately employed for the preparation of reference solid electrodes. The weight of each composition was about 0.5 g.

| COMPOSITION OF REFERENCE SOLID ELECTRODE (% by weight) | | | |
|---|---|---|---|
| Specimen No. | Carbonyl iron | α-Al₂O₃ | Platinum |
| 17-1 | 99 | 0 | 1 |
| 17-2 | 89 | 10 | 1 |
| 17-3 | 69 | 30 | 1 |
| 17-4 | 49 | 50 | 1 |

Figure 5:
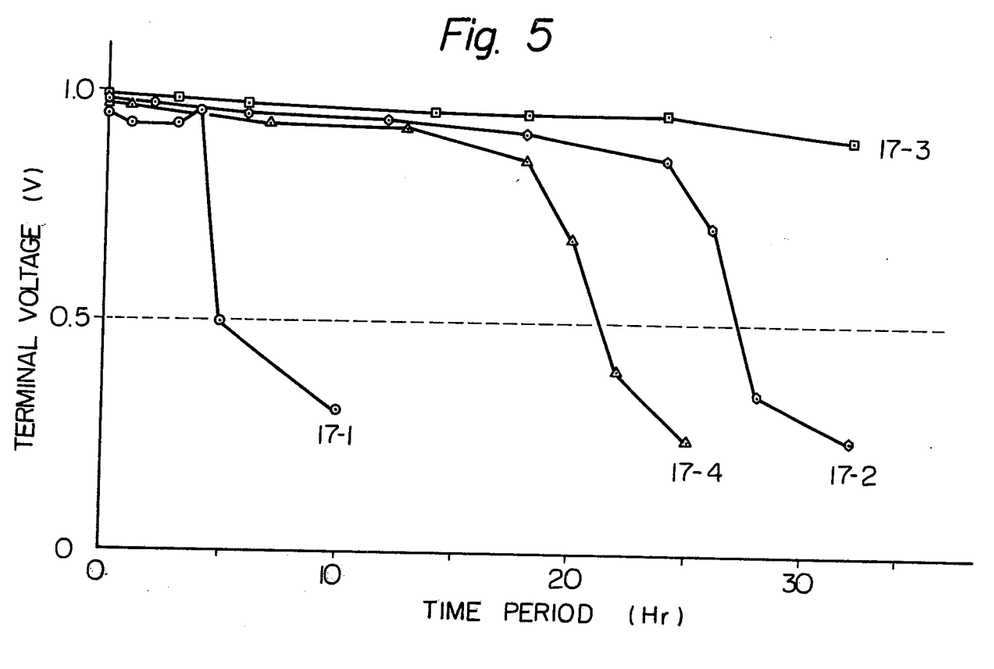
FIG. 5 is a graph showing the service durability of an oxygen sensing element.

Each oxygen sensing element was given a load of 1K-ohm and maintained at a temperature of 800° C. in an air atmosphere by using an electric oven, and under such conditions, its terminal voltage was measured. The results are shown in FIG. 5. The period of time for which the terminal voltage was reduced to 0.5 volt was as follows.

| HIGH TEMPERATURE DURABILITY | |
| --- | --- |
| Specimen No. | Time period (hours) |
| 17-1 | 5 |
| 17-2 | 27 |
| 17-3 | Longer than 30 |
| 17-4 | 25 |

What we claim is:

1. An improvement in an oxygen sensing element which comprises a solid electrolyte member composed of sintered material, and a means for providing a reference oxygen partial pressure, composed of a sintered product of a finely divided metal or metal-metal oxide powder, said means being completely embedded within the solid electrolyte member and having a lead-out wire connected thereto, and said solid electrolyte member having an electrode or electrodes mounted on the exterior surface thereof, said improvement comprising said sintered product having dispersed therein a finely divided platinum group metal powder in an amount of from 0.5 to 10% by weight, based on the total weight of the sintered product.

2. An oxygen sensing element according to claim 1 wherein the platinum group metal is at least one metal selected from the group consisting of platinum, rhodium, palladium and iridium.

3. An oxygen sensing element according to claim 1 wherein said sintered product has dispersed therein a finely divided platinum powder in an amount of from 1.0 to 5.0% by weight based on the total weight of the sintered product.

4. An oxygen sensing element according to claim 1 wherein said sintered product has dispersed therein a finely divided platinum powder and a finely divided rhodium powder in amounts of from 1.0 to 5.0% by weight and not more than 2.0% by weight, respectively, based on the total weight of the sintered product.

5. An oxygen sensing element according to any one of claim 1 to 4 wherein said sintered product has dispersed therein, in addition to the finely divided platinum group metal powder, a finely divided antisintering material in an amount of from 5 to 70% by weight based on the total weight of the sintered product.

6. An oxygen sensing element according to claim 5 wherein said antisintering material is identical to that of the solid electrolyte.

7. An oxygen sensor device for determining the oxygen concentration in an exhaust gas from an automobile internal combustion engine, comprising:
 (1) an oxygen sensing element which comprises a solid electrolyte member composed of sintered material, and a means for providing a reference oxygen partial pressure, composed of a sintered product of a finely divided metal or metal-metal oxide powder, said means being completely embedded within the solid electrolyte member, said solid electrolyte member having an electrode or electrodes mounted on the external surface thereof, and said sintered product having dispersed therein a finely divided platinum group metal powder in an amount of from 0.5 to 10% by weight, based on the weight of the sintered product;
 (2) two lead-out wires for transmitting therethrough output signals from the reference oxygen partial pressure-providing means and the electrode or electrodes on the external surface of the solid electrolyte member, respectively, to an electrical measuring circuit, and;
 (3) a casing for protecting the oxygen sensing element, the casing having a plurality of perforations through which the exhaust gas is allowed to flow.

8. An oxygen sensing element according to claim 5 wherein said antisintering material is at least one material selected from the group consisting of alumina, alumina - magnesia, silica, alumina - silica and a material identical to that of the solid electrolyte.

9. An oxygen sensing element according to claim 8 wherein said antisintering material is zirconia, zirconia - yttria, zirconia - calcia or Zirconia - magnesia.

* * * * *

UNITED STATES PATENT AND TRADEMARK OFFICE
CERTIFICATE OF CORRECTION

PATENT NO. : 4,209,378
DATED : June 24, 1980

INVENTOR(S) : Hiroshi Shinohara, et al

It is certified that error appears in the above—identified patent and that said Letters Patent is hereby corrected as shown below:

Correct inventor's name from "Hiroshi Schinohara" to

--Hiroshi Shinohara--.

Col. 1, lines 7-8, change "oxygensensing" to --oxygen sensing--.

Col. 2, line 3, change "2O- $\rightarrow$ O2(or 2O) + 4e-" to

--2O-- $\rightarrow$ O2(or 2O) + 4e- --.

Col. 4, line 17, change "ormore" to --or more--.

Signed and Sealed this

Eighteenth Day of November 1980

[SEAL]

Attest:

SIDNEY A. DIAMOND

Attesting Officer

Commissioner of Patents and Trademarks